United States Patent [19]

Rempfler et al.

[11] Patent Number: 4,894,083
[45] Date of Patent: Jan. 16, 1990

[54] HERBICIDAL EPOXIDES

[75] Inventors: Hermann Rempfler, Ettingen; Walter Kunz, Oberwil, both of Switzerland

[73] Assignee: Ciba-Geigy Corporation, Ardsley, N.Y.

[21] Appl. No.: 161,812

[22] Filed: Feb. 29, 1988

Related U.S. Application Data

[63] Continuation-in-part of Ser. No. 934,298, Nov. 24, 1986, Pat. No. 4,849,007.

[30] Foreign Application Priority Data

Dec. 2, 1985 [CH] Switzerland .................. 5131/85
Jun. 30, 1986 [CH] Switzerland .................. 2617/86

[51] Int. Cl.$^4$ ............... A01N 43/20; C07D 303/32
[52] U.S. Cl. .................................. 71/88; 549/548
[58] Field of Search ..................... 549/548; 71/88

[56] References Cited

U.S. PATENT DOCUMENTS

| | | | |
|---|---|---|---|
| 3,501,503 | 3/1970 | Cragoe, Jr. et al. | 549/548 |
| 3,719,465 | 3/1973 | Ozretich | 71/88 |
| 3,933,472 | 1/1976 | Buckman et al. | 71/121 |
| 4,211,549 | 7/1980 | Markley et al. | 71/88 |
| 4,490,165 | 12/1984 | Spatz et al. | 71/88 |

FOREIGN PATENT DOCUMENTS

| | | |
|---|---|---|
| 1210404 | 8/1986 | Canada. |
| 0117578 | 2/1984 | European Pat. Off. |
| 0114567 | 8/1984 | European Pat. Off. |
| 0138085 | 9/1984 | European Pat. Off. |
| 2520165 | 11/1976 | Fed. Rep. of Germany. |

OTHER PUBLICATIONS

J. Am. Chem. 87, pp. 1353-1364, (1965), Corey et al.
Chem. Ber. 91, pp. 2710-2719, (1953), B. Eistert et al.

*Primary Examiner*—Richard L. Raymond
*Attorney, Agent, or Firm*—Kevin T. Mansfield; Edward McC. Roberts

[57] ABSTRACT

The invention relates to a herbicidal and plant growth regulating composition which contains as active ingredient a 2-benzoyl-2-phenyloxirane of formula I

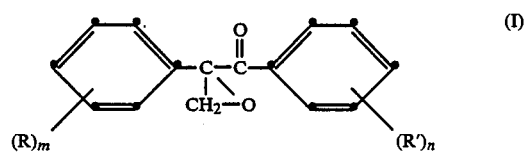

wherein each of m and n independently of the other is 0, 1, 2 or 3 and each of R and R' independently of the other is a halogen atom, a $C_1$-$C_4$alkyl, $C_1$-$C_4$alkoxy, $C_1$-$C_4$haloalkyl or $C_1$-$C_4$haloalkoxy group or the nitro or cyano group or a phenoxy group which is substituted by (R)$_m$, in the form of a racemate or an optically active enantiomer.

Some oxiranes are known as intermediates for the preparation of fungicides and others are novel. The herbicidal composition has selective action in rice crops and is active against grasses.

12 Claims, No Drawings

HERBICIDAL EPOXIDES

CROSS-REFERENCE TO RELATED APPLICATIONS

This is a continuation-in-part of our copending application, Ser. No. 934,298 filed Nov. 24, 1986 now U.S. Pat. No. 4,849,007.

The present invention relates to a herbicidal and plant growth regulating composition which contains epoxides as active ingredients, and to the use of this composition or of said epoxides for selectively controlling weeds in crops of useful plants or for regulating, in particular inhibiting, plant growth.

The active ingredients are 2-benzoyl-2-phenyloxiranes of formula I

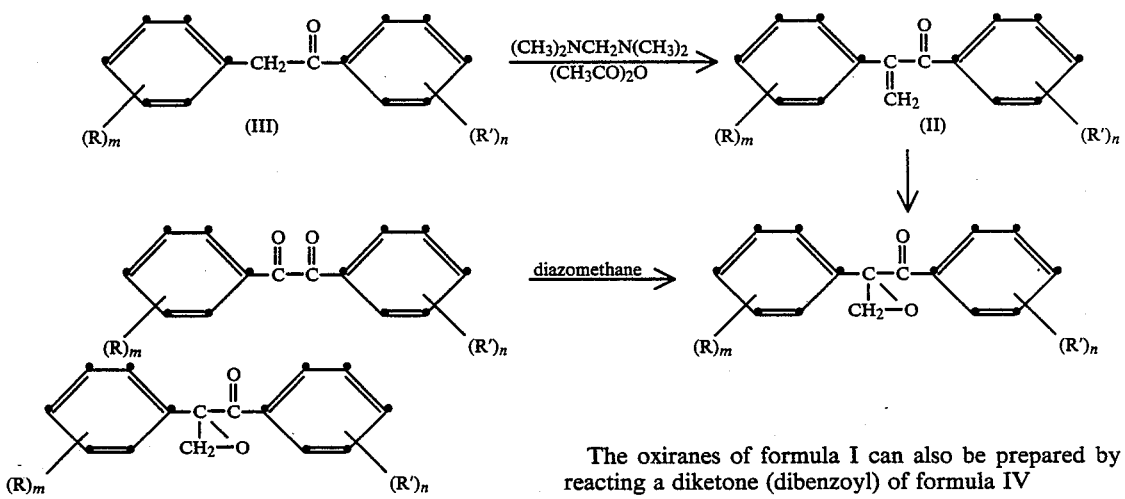

wherein each of m and n independently of the other is 0, 1, 2 or 3 and each of R and R' independently of the other is a halogen atom, a $C_1$-$C_4$alkyl, $C_1$-$C_4$alkoxy, $C_1$-$C_4$haloalkyl or $C_1$-$C_4$haloalkoxy group or the nitro or cyano group or a phenoxy group which is substituted by $(R)_m$, and the optically active enantiomers thereof.

Some of the 2-benzoyl-2-phenyloxiranes employed as active ingredients and the preparation thereof are known and described in Chem. Ber. 91 2710(1953) and in European patent applictions A 114 567 and A 117 578. These publications disclose the use of said 2-benzoyl-2-phenyloxiranes as intermediates for the preparation of fungicides.

The oxiranes of formula I are prepared in a manner known per se by epoxidising the styrene derivatives of formula II on which they are based

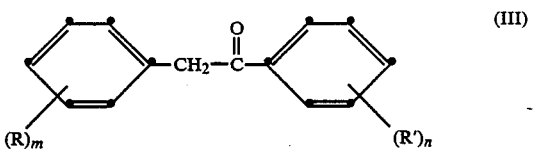

wherein m, n, R and R' are as defined for formula I.

Oxidation is effected for example with peracids such as peracetic acid, tert-butyl hydroperoxide, m-chloroperbenzoic acid, $H_2O_2$ etc., in the absence or presence of bases such as NaOH, KOH, $NaHCO_3$, in customary inert solvents. A carbonyl complex of transit metals, in particular $MO(CO)_6$, may be used as catalyst in said oxidation reactions.

The styrene derivatives of formula II can be obtained by reacting the corresponding ketones of formula III

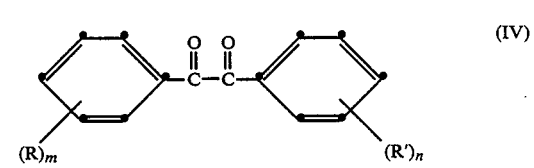

wherein m, n, R and R' are defined for formula I, with a dimethylmethyleneammonium halide in accordance with Ang. Chemie 1976 261 (q.v. also Heterocycles 12 (1979)938).

The reaction scheme can be represented as follows:

The oxiranes of formula I can also be prepared by reacting a diketone (dibenzoyl) of formula IV

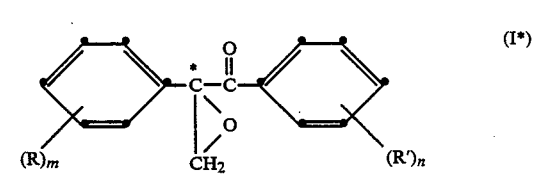

wherein m, n, R and R' are as defined for formula I, with diazomethane in the presence of a solvent and NaOH. (q.v. Chem. Ber. 91 (1958)2710 or J. Am. Chem. Soc. 87 (1965) 1353).

The oxiranes of this invention have a chiral carbon atom in the molecule and are obtained as racemates However, they can be resolved into their enantiomeric forms with relative ease by chromatography through acetyl cellulose. The individual enantiomers differ in activity and likewise constitute an object of the present invention.

Some oxiranes are known as intermediates for the preparation of fungicides and others are novel. The optically active enantiomers and the compounds of formula Ia

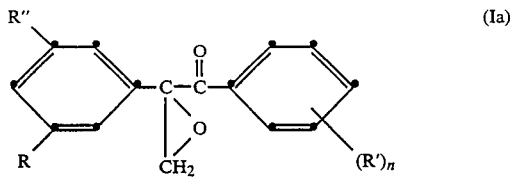

wherein R is halogen, $C_1$–$C_4$ alkyl or $C_1$–$C_4$ alkoxy, R" is hydrogen or has one of the meanings or R, and R' and n are as defined for formula I, in the form of a racemate or an optically active enantiomer, are novel.

Particularly active compounds are those wherein R" is hydrogen.

When preparing the above starting materials, intermediates and final products, one or more inert solvents or diluents may in principle be present, unless otherwise specifically stated. Examples of suitable solvents and diluents are aliphatic and aromatic hydrocarbons such as benzene, toluene, xylenes, petroleum ether; halogenated hydrocarbons such as chloroenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofuran; nitriles such as acetonitrile, propionitrile; N,N-dialkylated amides such as dimethylformamide; dimethyl sulfoxide; ketones such as acetone, diethyl ketone, methyl ethyl ketone, and mixtures of such solvents with one another.

Some of the oxiranes of formula I are known as intermediates for the preparation of fungicides. Surprisingly, it has been found that these compounds have herbicidal and plant growth regulating, in particular inhibiting, properties. They are suitable for use as selective herbicides in crops of useful plants, in particular in rice. They have pronounced activity especially against monocots, i.e. harmful grasses, whereas they cause no damage to crops of dicots or to species of cereals.

Particularly active compositions ar those which contain a 2-benzoyl-2-phenyl-oxirane of formula I, wherein each of m and n independently of the other is 0, 1, 2 or 3 and each of R and R' independently of the other is fluorine, chlorine, bromine, methyl, methoxy or trifluoromethyl, or R is also a phenoxy group which is substituted by (R)$_m$.

Compositions which are also active are those which contain as active ingredient a 2-benzoyl-2-phenyloxirane derivative of formula I, wherein each of m and n independently of the other is 0, 1, 2 or 3 and each of R and R' independently of the other is fluorine, chlorine, methyl, methoxy or trifluoromethyl.

Compounds of particular interest are:
2-benzoyl-2-phenyloxirane,
2-(4-bromobenzoyl-2-phenyl)oxirane,
2-(4-chlorobenzoyl)-2-(4-chlorophenyl) oxirane,
2-(4-chlorobenzoyl)-2-(2-chlorophenuyl)oxirane,
2-benzoyl-2-p-tolyloxirane,
2-(2-chlorobenzoyl)-2-phenyloxirane,
2-anisoyl-2- phenyloxirane,
2-(4-chlorobenzoyl)-2-(3-bromophenyl)oxirane and
2-(4-chlorobenzoyl)-2-phenyloxirane.

The compounds of formula I exhibit herbicidal and plant growth regulating, in particular inhibiting, activity. The are particularly active against monocots, i.e. grasses.

A great advantage resides in the fact that the novel compounds of formula I act selectively towards dicotyledenous cultivated plants and also towards monocots such as cereals, maize or rice, which means that they can be employed for controlling weeds in such crops.

The compounds of formula I are usually successfully applied at concentrations of 0.005 to 4 kg/ha, in particular 0.01 to 1 kg/ha.

When used at low rates of application, the compounds of formula I have good selective growth inhibiting and selective herbicidal properties which make them most suitable for use in crops of useful plants, preferably in cereals, cotton, soybeans, maize and rice. In some cases damage is also caused to weeds which have only been controlled up to now with total herbicides.

The compounds of formula I have in addition pronounced plant growth inhibiting properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth inhibitors resides in the fact that nutrients are able increasingly to promote flower formation and fruiting, whereas vegetative growth is inhibited.

At higher rates of application of compounds of formula I, all tested plants are so severely damaged in their development that they die.

The invention also relates to herbicidal and plant growth regulating compositions which contain a novel compound of formula I, and also to methods of controlling weeds pre- and postemergence and of inhibiting the growth of monocots and dicots, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic sufactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substitutents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, New Jersey, 1981; H Stache, "Tensid-Taschenbuch" (Handbook of Surfactants), C. Hanser Verlag, Munich & Vienna, 1981.

The herbicidal preparations usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| compound of formula I: | 1 to 20%, preferably 5 to 10% |
| surfactant: | 5 to 30%, preferably 10 to 20% |
| liquid carrier: | 50 to 94%, preferably 70 to 85% |
| Dusts | |
| compound of formula I: | 0.1 to 10%, preferably 0.1 to 1% |
| solid carrier: | 99.9 to 90%, preferably 99.9 to 99% |
| Suspension concentrates | |
| compound of formula I: | 5 to 75%, preferably 10 to 50% |
| water: | 94 to 25%, preferably 90 to 30% |
| surfactant: | 1 to 40%, preferably 2 to 30% |
| Wettable powders | |
| compound of formula I: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| compound of formula I: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% of active ingredient. The rates of application are usually from 0.005 to 5 kg a.i./ha.

The compositions may also contain further ingredients such as stabilisers, antifoams, viscosity regulators, binders, tackifiers, as well as fertilisers and other compounds for obtaining special effects.

The invention is illustrated in more detail by the following non-limitative Examples. Percentages are by weight.

EXAMPLE 1

Preparation of 1-benzoyl-1-(2,4-dichlorophenyl)oxirane

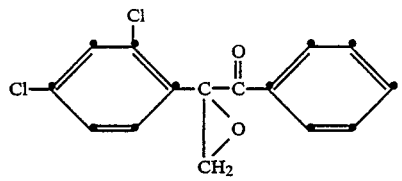

With stirring, 22.2 ml of 30% hydrogen peroxide are added dropwise to 16.5 g of 2-(2,4-dichlorophenyl)-3-phenylprop-1-en-3-one in 225 ml of methanol, followed by the dropwise addition of 12.4 l of 3N sodium hydroxide solution over ¾ hour at a maximum temperature of +3° C., with cooling. The reaction mixture is stirred for a further 5 hours, decomposed with ice/water and extracted with methylene chloride. The extracts are washed with water and sodium hydrogen sulfite (peroxide test) and concentrated in vacuo and dried, affording 7.3 g of crude epoxide which is purified by high vacuum distillation.

EXAMPLE 2

Preparation of 2-(2,4-dichlorobenzoyl)-2-(2,4-dichlorophenyl)oxirane

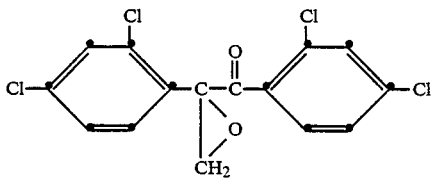

With cooling and stirring, an ethereal diazomethane solution prepared from 3.1 g of nitrosomethylurea and aqueous sodium hydroxide solution in ether is added dropwise to a solution of 3.4 g of 2,2',4,4'-tetrachlorobenzil in 50 ml of dioxane. When the dropwise addition is complete, stirring is continued for 16 hours at room temperature, and the reaction mixture is then concentrated to dryness. The residual oil is crude 2-(2,4-dichlorobenzoyl)-2-(2,4-dichlorophenyl)oxirane which is purified by high vacuum distillation.

EXAMPLE 3

Preparation of 2-(4-chlorobenzoyl)-2-(4-chlorophenyl)oxirane

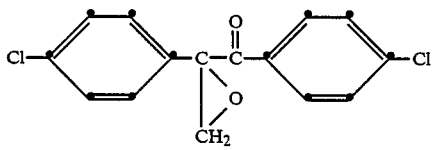

With cooling and stirring, an ethereal diazomethane solution prepared by reaction of 5.34 g of N-nitrosomethylurea with aqueous sodium hydroxide solution in ether is added dropwise to a solution of 5 g of 4,4'-dichlorobenzil in 50 ml of dioxane. When the dropwise addition is complete, stirring is continued for 16 hours at room temperature, and the reaction solution is then concentrated by evaporation. The residual oil is crude 2-(4-chlorobenzoyl)-2-(4-chlorophenyl)oxirane which is purified by high vacuum distillation.

EXAMPLE 4

Preparation of 2-(4-chlorobenzoyl)-2-(4-chlorophenyl)oxirane

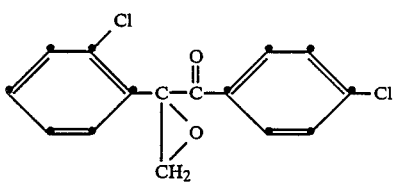

1 ml of 10% sodium hydroxide and 1 ml of 30% hydrogen peroxide are added to a solution of 150 mg of 1-(4-chlorobenzoyl)-2'-chlorostyrene in 8 ml of methanol. The reaction mixture is then left to stand for 14 hours at room temperature and then concentrated in vacuo. The residue is taken up in methylene chloride, and the resultant solution is washed, dried over sodium sulfate and concentrated in vacuo. The residue is purified through a column of silica gel with methylene chloride as eluant. The eluate is concentrated, and the residue is triturated with petroleum ether, affording 25 mg of crystalline 2-(4-chlorobenzoyl)-2-(2-chlorophenyl)oxirane which melts at 65°-66° C.

The starting 1-(4-chlorobenzoyl)-2-chlorostyrene is prepared as follows:

1 ml of acetic anhydride and 1 ml of tetramethyldiaminoethane are added to 500 mg of 4-chloro-2-(2-chlorophenyl)acetophenone, and the solution obtained is stirred for 30 minutes at room temperature. The reaction mixture is then concentrated, the residue is taken up in a small amount of methanol, and the resultant solution is concentrated. The residue is triturated in petroleum ether, affording 280 mg of 1-(4-chlorobenzoyl)-2-chlorostyrene which has a melting point of 120°-122° C.

The compounds listed in Table 1 are prepared by procedures analogous to those of these Examples.

TABLE 1

| Comp. | (R)$_m$ | (R$^1$)$_n$ | physical data |
|---|---|---|---|
| 1.001 | H | H | oil |
| 1.002 | 4-Cl | 4-OCH$_3$ | oil |
| 1.003 | 4-Cl | 4-CH$_3$ | n$_D^{30}$ 1.5870 |
| 1.004 | 4-Cl | 4-CF$_3$ | oil |
| 1.005 | 4-Cl | 4-Br | n$_D^{25}$ 1.6132 |
| 1.006 | 4-Cl | H | S.p. 150-155° C./0.02 mbar n$_D^{25}$ 1.5885 |
| 1.007 | 4-Cl | 2-Cl | oil |
| 1.008 | 4-Cl | 2-Cl | oil |
| 1.009 | 4-Cl | 3-Cl | |
| 1.010 | 4-Cl | 4-Cl | n$_D^{30}$ 1.5994 Example 3 |
| 1.011 | 4-Cl | 3,4 Cl$_2$ | n$_D^{30}$ 1.6120 |
| 1.012 | 4-Cl | 2-CH$_3$ | n$_D^{25}$ 1.5840 |
| 1.013 | 4-Cl | 2-F | b.p. 150° C./0.003 mbar n$_D^{25}$ 1.5875 |
| 1.014 | 4-Br | H | n$_D^{32}$ 1.6062 |
| 1.015 | 4-Br | 4-Cl | n$_D^{30}$ 1.6110 |
| 1.016 | 4-F | H | oil |

TABLE 1-continued

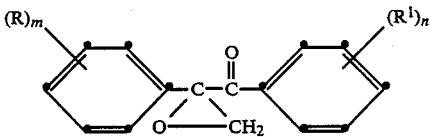

| Comp. | $(R)_m$ | $(R^1)_n$ | physical data |
|---|---|---|---|
| 1.017 | 4-F | 4-Cl | oil |
| 1.018 | 4-CH₃ | H | $n_D^{20}$ 1.5792 |
| 1.019 | 4-CH₃ | 4-Cl | $n_D^{25}$ 1.5880 |
| 1.020 | 4-CH₃ | 4-CH₃ | $n_D^{26}$ 1.5750 |
| 1.021 | 4-OCH₃ | H | $n_D^{26}$ 1.5943 |
| 1.022 | 4-OCH₃ | 2-Cl | $n_D^{30}$ 1.5745 |
| 1.023 | 2,4 Cl₂ | 2-Cl | $n_D^{25}$ 1.5770 |
| 1.024 | 2,4 Cl₂ | 2-CH₃ | $n_D^{25}$ 1.5790 |
| 1.025 | 2,6 Cl₂ | 2-Cl | m.p. 114–115° C. |
| 1.026 | 3,4 Cl₂ | 2-Cl | $n_D^{24}$ 1.5900 |
| 1.027 | 2-Cl | H | $n_D^{31}$ 1.5801 |
| 1.028 | 2-Cl | 4-Cl | m.p. 65–66° C. Example 4 |
| 1.029 | 3-Cl | H | $n_D^{25}$ 1.5960 |
| 1.030 | 3-Cl | 4-Cl | m.p. 79–81° C. |
| 1.031 | 3-Cl | 3-Cl | $n_D^{30}$ 1.5977 |
| 1.032 | 3-Cl | 4-CH₃ | $n_D^{25}$ 1.5860 |
| 1.033 | 3-CF₃ | 4-Cl | $n_D^{25}$ 1.5367 |
| 1.034 | 3-Cl | 2-OCH₃ | $n_D^{25}$ 1.5772 |
| 1.035 | 3,5 Cl₂ | 3,6 Cl₂ 4-Cl | $n_D^{25}$ 1.6055 |
| 1.036 | 3-CH₃ | H | $n_D^{30}$ 1.5810 |
| 1.037 | 3-CH₃ | 4-CH₃ | $n_D^{30}$ 1.5770 |
| 1.038 | 3-CH₃ | 4-Cl | m.p. 60–62° C. |
| 1.039 | 2-Cl | 2,4 Cl₂ | $n_D^{24}$ 1.5824 |
| 1.040 | H | 2-Cl | $n_D^{30}$ 1.5823 |
| 1.041 | H | 3-Cl | oil |
| 1.042 | H | 4-Cl | $n_D^{30}$ 1.5757 |
| 1.043 | H | 4-OCH₃ | m.p. 76–78° C. |
| 1.044 | 2,4 Cl₂ | H | oil Example 1 |
| 1.045 | 2,4 Cl₂ | 2,4 (CH₃)₂ | oil |
| 1.046 | 2,4 Cl₂ | 4-CH₃ | oil |
| 1.047 | 2,4 Cl₂ | 2,4 Cl₂ | oil Example 2 |
| 1.048 | 2,4 Cl₂ | 4-Cl | $n_D^{22}$ 1.6045 |
| 1.049 | 4-CH₃ | 3-Cl | $n_D^{26}$ 1.5800 |
| 1.050 | 4-CH₃ | 3-CH₃ | $n_D^{26}$ 1.5630 |
| 1.051 | 4-CH₃ | 2-Cl | $n_D^{25}$ 1.5845 |
| 1.052 | 4-CH(CH₃)₂ | H | |
| 1.053 | 4-CN | 4-Cl | |
| 1.054 | 3-Cl | 2,6 Cl₂ | $n_D^{25}$ 1.5660 |
| 1.055 | 3-Cl | 3-CH₃ | |
| 1.056 | 3-Cl | 4-NO₂ | |
| 1.057 | 3-Cl | 2-Cl | $n_D^{25}$ 1.5930 |
| 1.058 | 3-Br | 4-Cl | $n_D^{25}$ 1.6170 |
| 1.059 | 2-CH₃ | H | $n_D^{25}$ 1.5838 |
| 1.060 | 2-OCH₃ | H | $n_D^{25}$ 1.5803 |
| 1.061 | 2-OCH₃ | 4-Cl | $n_D^{25}$ 1.5835 |
| 1.062 | 3,4(OCH₃)₂ | 4-Cl | |
| 1.063 | 3,4(OCH₃)₂ | H | |
| 1.064 | 3-Cl, 5-CH₃ | 4-Cl | $n_D^{25}$ 1.5923 |
| 1.065 | 4-(2-chloro-4-trifluoromethylphenoxy) | 4-Cl | |
| 1.066 | 4-(3-trifluoromethylphenoxy) | 4-Cl | |
| 1.067 | 3-(2-chloro-4-trifluoromethylphenoxy) | 4-Cl | |
| 1.068 | 4(2,4-dichlorophenoxy) | 4-Cl | |
| 1.069 | 2-chloro-4-(2-chloro-4-trifluoromethylphenoxy) | 2-Cl | $n_D^{35}$ 1.5616 |
| 1.070 | 3-(4-trifluoromethylphenoxy) | H | m.p. 96–97° C. |
| 1.071 | 4-(2-chloro-4-trifluoromethylphenoxy) | H | $n_D^{30}$ 1.5658 |
| 1.072 | 4-(3-trifluoromethylphenoxy) | H | $n_D^{35}$ 1.5608 |
| 1.073 | H | 2,4-Cl₂ | $n_D^{30}$ 1.5905 |

TABLE 1-continued

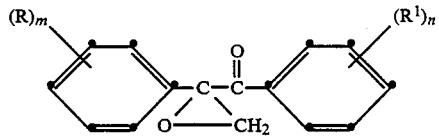

| Comp. | $(R)_m$ | $(R^1)_n$ | physical data |
|---|---|---|---|
| 1.074 | 3-CH₃ | 2,3-(CH₃)₂ | m.p. 60–63° C. |
| 1.075 | 3-CH₃ | 2-Cl | $n_D^{25}$ 1.5825 |
| 1.076 | 3-CH₃ | 4-F | $n_D^{25}$ 1.5657 |
| 1.077 | 3-CH₃ | 2-CH₃ | $n_D^{30}$ 1.5615 |
| 1.078 | 3-Cl | 2,3-(CH₃)₂ | $n_D^{25}$ 1.5832 |
| 1.079 | 3-Cl | 2-F | $n_D^{30}$ 1.5805 |
| 1.080 | 3-Cl | 4-F | $n_D^{30}$ 1.5780 |
| 1.081 | 3-F | 4-Cl | m.p. 59–60° C. |
| 1.082 | 3-F | H | $n_D^{24}$ 1.5675 |
| 1.083 | 3-OCH₃ | 4-Cl | m.p. 71° C. |
| 1.084 | 3-OCH₃ | H | $n_D^{25}$ 1.5833 |
| 1.085 | 3-OC₃H₇(n) | H | $n_D^{25}$ 1.5660 |
| 1.086 | 3-OC₃H₇(n) | 4-Cl | $n_D^{25}$ 1.5724 |
| 1.087 | 2-Br, 5-OC₃H₇(n) | H | $n_D^{27}$ 1.5838 |
| 1.088 | 4-SO₂CH₃ | 4-Cl | m.p. 124–26° C. |
| 1.089 | 2,4-Cl₂ | 2-F | $n_D^{30}$ 1.5791 |
| 1.090 | 2-F, 6-Cl | 2-Cl | m.p. 102–104° C. |
| 1.091 | 2,4-Cl₂ | 2-CF₃ | $n_D^{30}$ 1.5239 |
| 1.092 | 2,4-Cl₂ | 2-OCH₃ | |
| 1.093 | 2,6-Cl₂ | H | m.p. 66–68° C. |
| 1.094 | 2-F, 6-Cl | 2-F | |
| 1.095 | 3-CF₃ | H | $n_D^{30}$ 1.5260 |
| 1.096 | 2-Cl, 4-OCH₃ | 4-Cl | $n_D^{30}$ 1.5875 |
| 1.097 | 2-Cl, 4-OCH₃ | 2-CH₃ | $n_D^{30}$ 1.5687 |
| 1.098 | 2-Cl, 4-OCH₃ | 2-Cl | $n_D^{30}$ 1.5759 |
| 1.099 | 3-Cl | 4-CN | |
| 1.100 | 3,5-Cl₂ | H | |
| 1.101 | 3-Cl | 4-Cl | (R)-enantiomer $[\alpha]_D = +196.6°$ (1% in CHCl₃) |
| 1.102 | 3-Cl | 4-Cl | (S)-enantiomer $[\alpha]_D = -157°$ (1% in CHCl₃) |
| 1.103 | 3-CH₃ | 2-F | $n_D^{30}$ 1.5526 |
| 1.104 | 3-OCH₃ | 2-F | $n_D^{30}$ 1.5554 |
| 1.105 | 3-F | 2-F | $n_D^{30}$ 1.5436 |
| 1.106 | 4-OCF₃ | 2-F | $n_D^{30}$ 1.5100 |
| 1.107 | 3-CH₃ | 3-F | $n_D^{24}$ 1.5590 |
| 1.108 | 3-F | 4-CH₃ | $n_D^{25}$ 1.5657 |
| 1.109 | 3-F | 4-F | $n_D^{30}$ 1.5402 |
| 1.110 | 4-OCF₃ | H | $n_D^{25}$ 1.5165 |
| 1.111 | 2-Cl; 4-CH₃ | H | m.p. 57–60° |
| 1.112 | 3-Cl; 4-CH₃ | H | $n_D^{25}$ 1.5938 |
| 1.113 | 3-F; 5-CH₃ | H | $n_D^{23}$ 1.5600 |
| 1.114 | 3-Cl; 6-F | 2-Cl | $n_D^{25}$ 1.5708 |
| 1.115 | 3-Br | H | $n_D^{30}$ 1.5968 |
| 1.116 | 3-Br | 2-F | $n_D^{30}$ 1.5713 |
| 1.117 | 3-F; 5-CH₃ | 2-Cl | $n_D^{30}$ 1.5600 |
| 1.118 | 3-Cl; 6-F | 2-F | $n_D^{25}$ 1.5712 |
| 1.119 | 3-Cl; 4-F | H | $n_D^{25}$ 1.5793 |
| 1.120 | 3-Cl; 4-F | 2-F | $n_D^{25}$ 1.5657 |
| 1.121 | 2,4-F₂ | 2-F | $n_D^{25}$ 1.5378 |
| 1.122 | 3-F; 6-F | 2-F | m.p. 70–71° |
| 1.123 | 2-F; 3-CH₃ | H | m.p. 51–53° |
| 1.124 | 2-F; 3-CH₃ | 2-F | m.p. 106–108° |
| 1.125 | 2,6-F₂ | 2-F | m.p. 73–74° |
| 1.126 | 2-F | 2-Cl | $n_D^{30}$ 1.5671 |
| 1.127 | 3-F | 2,4-Cl₂ | $n_D^{25}$ 1.5881 |
| 1.128 | 3-F | 2-Cl | $n_D^{25}$ 1.5706 |
| 1.129 | 3,4-F₂ | 2-F | $n_D^{25}$ 1.5425 |
| 1.130 | 3,5-F₂ | 2-F | $n_D^{25}$ 1.5466 |
| 1.131 | 3,4-F₂ | H | $n_D^{25}$ 1.5538 |
| 1.132 | 3,5-F₂ | H | $n_D^{25}$ 1.5561 |
| 1.133 | 3-CH₃ | 2,4-Cl₂ | $n_D^{25}$ 1.5981 |
| 1.134 | 3-phenoxy | H | $n_D^{30}$ 1.6035 |
| 1.135 | 3-F | 2-F; 4-Cl | $n_D^{30}$ 1.5629 |
| 1.136 | 3-phenoxy | 4-Cl | $n_D^{30}$ 1.5734 |
| 1.137 | 3-F | 2,6-F₂ | $n_D^{30}$ 1.5330 |
| 1.138 | 3-phenoxy | 2-F | $n_D^{25}$ 1.5927 |
| 1.139 | 3-F | 3-Br | $n_D^{26}$ 1.5827 |
| 1.140 | 3-F | 2-Br | $n_D^{25}$ 1.5840 |
| 1.141 | 3-F | 2-CH₃ | $n_D^{25}$ 1.5558 |

TABLE 1-continued

[Structure: diphenyl compound with (R)m on left ring, (R¹)n on right ring, connected via -C(=O)-C(-O-CH2-)]

| Comp. | (R)m | (R¹)n | physical data |
|---|---|---|---|
| 1.142 | 3-C₂H₅ | H | $n_D^{30}$ 1.5753 |
| 1.143 | 4-F | 2-Cl | $n_D^{26}$ 1.5711 |
| 1.144 | 4-F | 2-F | $n_D^{26}$ 1.5542 |
| 1.145 | 4-CH₃ | 2-CH₃ | $n_D^{30}$ 1.5452 |

Formulation Examples

EXAMPLE 5

Formulation Examples for compounds of formula I
(percentages are by weight)

| (a) Wettable powders | (a) | (b) | (c) |
|---|---|---|---|
| compound of Table 1 | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| compound of Table 1 | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of Table 1 | 0.1% | 1% |
| talcum | 99.9% | — |
| kaolin | — | 99% |

Dusts which are ready for use are obtained by mixing the active ingredient with the carrier, and grinding the mixture in a suitable mill.

| (d) Extruder granulates | (a) | (b) |
|---|---|---|
| compound of Table 1 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of Table 1 | 3% |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrates | (a) | (b) |
|---|---|---|
| compound of Table 1 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of Table 1 | 5% |
| isopropylamine | 1% |
| octylphenol polyethylene glycol ether (78 moles of ethylene oxide) | 3% |
| water | 91% |

Biological Examples

EXAMPLE 6

Preemergence herbicidal action

Preemergence selective herbicidal action in cereals and maize

In a greenhouse, seeds of barley, wheat, maize and of 10 weeds are sown in flower pots (brim diameter: 11 cm) filled with sterile soil. Immediately after sowing the test plants, the surface of the soil is treated with an aqueous dispersion of the test compounds, obtained from a 25% emulsifiable concentrate. Concentrations of 4, 2 and 1 kg of test compound per hectare are applied. The pots are then kept in the greenhouse at 22°–25° C. and 50–70% relative humidity, and the plants are watered regularly. The test is evaluated 3 weeks later and the condition of the plants is assessed in accordance with the following rating:
1 = plant has not germinated or it has dried
2–3 = very strong herbicidal action
4–6 = moderate action
7–8 = weak action
9 = no action, plant grows as untreated controls
— = no test made.
The results are shown in Table 2.

TABLE 2

| Compound | Barley 4 | Barley 2 | Barley 1 | Wheat 4 | Wheat 2 | Wheat 1 | Maize 4 | Maize 2 | Maize 1 | Lolium perenne 4 | Lolium perenne 2 | Lolium perenne 1 | Alopecurus myos. 4 | Alopecurus myos. 2 | Alopecurus myos. 1 | Digitaria sanguinalis 4 | Digitaria sanguinalis 2 | Digitaria sanguinalis 1 | Echinochloa crus galli 4 | Echinochloa crus galli 2 | Echinochloa crus galli 1 | Sorghum halepense 4 | Sorghum halepense 2 | Sorghum halepense 1 | Rottboellia exaltata 4 | Rottboellia exaltata 2 | Rottboellia exaltata 1 |
|---|---|---|---|---|---|---|---|---|---|---|---|---|---|---|---|---|---|---|---|---|---|---|---|---|---|---|---|
| 1.006 | 9 | 9 | 9 | 8 | 9 | 9 | 8 | 9 | 9 | 3 | 6 | 9 | 9 | 9 | 9 | 1 | 1 | 1 | 1 | 1 | 2 | 7 | 8 | 9 | 3 | 8 | 9 |
| 1.018 | 9 | 9 | 9 | 9 | 9 | 9 | 9 | 9 | 9 | 2 | 6 | 6 | 9 | 9 | 9 | 1 | 1 | 1 | 1 | 1 | 3 | 5 | 9 | 9 | 3 | 3 | 7 |
| 1.019 | 9 | 9 | 9 | 9 | 9 | 9 | 9 | 9 | 9 | 7 | 8 | 9 | 8 | 9 | 9 | 1 | 1 | 2 | 2 | 2 | 5 | 9 | 9 | 9 | 7 | 9 | 9 |
| 1.029 | 7 | 8 | 9 | 8 | 9 | 9 | 7 | 9 | 9 | 3 | 3 | 5 | 2 | 4 | 6 | 1 | 1 | 1 | 1 | 1 | 4 | 2 | 4 | 6 | 3 | 3 | 6 |
| 1.032 | 9 | 9 | 9 | 9 | 9 | 9 | 7 | 8 | 9 | 7 | 8 | 9 | 3 | 4 | 6 | 1 | 1 | 1 | 1 | 1 | 1 | 9 | 9 | 9 | 4 | 6 | 9 |
| 1.036 | 4 | 5 | 8 | 6 | 8 | 9 | 4 | 7 | 8 | 1 | 1 | 3 | 2 | 2 | 3 | 1 | 1 | 1 | 1 | 1 | 1 | 2 | 2 | 4 | 1 | 2 | 2 |
| 1.037 | 2 | 7 | 9 | 8 | 9 | 9 | 7 | 8 | 9 | 3 | 5 | 8 | 1 | 1 | 3 | 1 | 1 | 1 | 1 | 1 | 3 | 3 | 3 | 5 | 1 | 1 | 2 |
| 1.038 | 6 | 7 | 9 | 7 | 9 | 9 | 7 | 8 | 9 | 1 | 2 | 4 | 1 | 4 | 6 | 1 | 1 | 1 | 1 | 1 | 1 | 1 | 2 | 7 | 1 | 4 | 6 |
| 1.040 | 7 | 9 | 9 | 8 | 9 | 9 | 4 | 5 | 8 | 2 | 2 | 2 | 1 | 2 | 4 | 1 | 1 | 1 | 2 | 3 | 4 | 1 | 2 | 4 | 1 | 1 | 2 |
| 1.042 | 9 | 9 | 9 | 8 | 9 | 9 | 9 | 9 | 9 | 4 | 6 | 7 | 1 | 3 | 8 | 1 | 1 | 1 | 1 | 1 | 2 | 1 | 6 | 9 | 2 | 3 | 4 |
| 1.050 | 9 | 9 | 9 | 9 | 9 | 9 | 9 | 9 | 9 | 2 | 4 | 5 | 7 | 9 | 9 | 1 | 1 | 4 | 1 | 1 | 2 | 9 | 9 | 9 | 7 | 9 | 9 |
| 1.051 | 9 | 9 | 9 | 9 | 9 | 9 | 9 | 9 | 9 | 4 | 4 | 7 | 8 | 9 | 9 | 1 | 2 | 2 | 1 | 1 | 2 | 1 | 3 | 4 | 5 | 6 | 8 |
| 1.058 | 9 | 9 | 9 | 8 | 9 | 9 | 8 | 9 | 9 | 4 | 4 | 6 | 5 | 6 | 6 | 1 | 1 | 2 | 1 | 2 | 4 | 7 | 9 | 9 | 6 | 7 | 9 |
| 1.073 | 9 | 9 | 9 | 9 | 9 | 9 | 6 | 7 | 9 | 5 | 6 | 8 | 1 | 4 | 4 | 1 | 1 | 1 | 1 | 1 | 1 | 2 | 2 | 4 | 1 | 3 | 3 |
| 1.079 | 7 | 8 | 9 | 6 | 7 | 9 | 3 | 4 | 7 | 1 | 1 | 5 | 1 | 2 | 4 | 1 | 1 | 1 | 1 | 1 | 1 | 1 | 3 | 1 | 1 | 1 | 2 |
| 1.080 | 7 | 9 | 9 | 7 | 8 | 9 | 4 | 5 | 7 | 1 | 3 | 5 | 1 | 4 | 8 | 1 | 1 | 1 | 1 | 1 | 4 | 2 | 2 | 6 | 1 | 3 | 3 |
| 1.104 | 2 | 5 | 7 | 5 | 6 | 8 | 3 | 3 | 4 | 1 | 1 | 1 | 1 | 1 | 2 | 1 | 1 | 1 | 1 | 1 | 1 | 1 | 1 | 3 | 1 | 1 | 1 |
| 1.107 | 4 | 6 | 8 | 6 | 8 | 9 | 7 | 7 | 9 | 1 | 1 | 3 | 1 | 1 | 3 | 1 | 1 | 1 | 1 | 1 | 1 | 1 | 4 | 5 | 1 | 2 | 4 |
| 1.108 | 7 | 9 | 9 | 7 | 8 | 9 | 8 | 9 | 9 | 1 | 3 | 5 | 4 | 5 | 7 | 1 | 1 | 1 | 1 | 1 | 1 | 6 | 7 | 1 | 2 | 4 |
| 1.109 | 7 | 7 | 9 | 7 | 9 | 9 | 6 | 7 | 9 | 1 | 4 | 5 | 5 | 7 | 8 | 1 | 1 | 1 | 1 | 1 | 1 | 1 | 6 | 1 | 2 | 3 |
| 1.113 | 6 | 7 | 8 | 7 | 7 | 8 | 7 | 8 | 9 | 2 | 3 | 6 | 3 | 3 | 5 | 1 | 1 | 1 | 1 | 1 | 1 | 4 | 5 | 1 | 1 | 1 |
| 1.116 | 9 | 9 | 9 | 9 | 9 | 9 | 7 | 7 | 9 | 6 | 7 | 9 | 4 | 6 | 8 | 1 | 1 | 3 | 2 | 4 | 7 | 7 | 8 | 9 | 2 | 3 | 5 |
| 1.117 | 9 | 9 | 9 | 9 | 9 | 9 | 7 | 7 | 9 | 7 | 7 | 9 | 5 | 7 | 8 | 2 | 2 | 3 | 3 | 6 | 9 | 8 | 9 | 9 | 2 | 4 | 5 |
| 1.119 | 8 | 9 | 9 | 9 | 9 | 9 | 8 | 9 | 9 | 4 | 7 | 7 | 6 | 7 | 9 | 1 | 1 | 1 | 1 | 1 | 4 | 4 | 9 | 9 | 1 | 3 | 5 |
| 1.120 | 9 | 9 | 9 | 9 | 9 | 9 | 6 | 9 | 9 | 5 | 7 | 9 | 5 | 5 | 8 | 1 | 1 | 1 | 1 | 1 | 2 | 5 | 5 | 7 | 2 | 4 | 5 |
| 1.122 | 7 | 8 | 9 | 7 | 8 | 9 | 5 | 5 | 8 | 4 | 6 | 6 | 7 | 8 | 9 | 1 | 1 | 1 | 2 | 2 | 2 | 1 | 4 | 4 | 1 | 1 | 1 |
| 1.127 | 9 | 9 | 9 | 9 | 9 | 9 | 8 | 9 | 9 | 4 | 9 | 9 | 8 | 8 | 9 | 1 | 1 | 1 | 1 | 1 | 1 | 4 | 4 | 8 | 1 | 2 | 4 |
| 1.128 | 9 | 9 | 9 | 9 | 9 | 9 | 4 | 5 | 7 | 4 | 4 | 6 | 4 | 5 | 7 | 1 | 1 | 1 | 1 | 1 | 3 | 1 | 1 | 2 | 1 | 1 | 2 |
| 1.131 | 8 | 9 | 9 | 8 | 9 | 9 | 9 | 9 | 9 | 4 | 6 | 9 | 8 | 9 | 9 | 1 | 1 | 1 | 1 | 1 | 1 | 5 | 8 | 9 | 1 | 2 | 3 |
| 1.132 | 8 | 9 | 9 | 8 | 9 | 9 | 6 | 8 | 9 | 1 | 3 | 7 | 4 | 5 | 7 | 1 | 1 | 1 | 1 | 1 | 2 | 2 | 4 | 1 | 1 | 3 |
| 1.135 | 9 | 9 | 9 | 9 | 9 | 9 | 8 | 9 | 9 | 7 | 8 | 9 | 7 | 9 | 9 | 1 | 3 | 3 | 1 | 2 | 2 | 3 | 4 | 6 | 2 | 3 | 4 |
| 1.144 | — | 5 | 8 | — | 5 | 5 | — | 5 | 6 | — | 1 | 1 | — | 1 | 2 | — | 1 | 1 | — | 1 | 1 | — | 1 | 1 | — | 1 | 1 |

The grasses are severely damaged; either slight damage or no damage at all is caused to the barley, wheat and maize.

EXAMPLE 7

Postemergence herbicidal action (contact herbicide)

A number of weeds, both mono- and dicotyledonous, are sprayed postemergence in the 4- to 6-leaf stage with an aqueous active ingredient dispersion at a rate of 4 kg of test compound per hectare and kept at 24°–26° C. and 45–60% relative humidity. The test is evaluated 15 days later in accordance with the same rating as employed above. In this test, the test compounds of Table 1 also exhibit stong to very strong herbicidal activity.

EXAMPLE 8

Preemergence herbicidal action

Plastic pots are filled with expanded vermiculite (density: 0.135 g/cm$^3$; water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: Nasturtium officinalis, Agrostis tenuis, Stellaria media and Digitaria sanguinalis. The pots are then kept in a climatic chamber at 20° C., an illumination of about 20 klux and a relative humidity of 70%. During the germinating phase of 4 to 6 days, the pots are covered with lightpermeable material and watered with deionised water to increase the local humidity. After the 5th day, 0,5% of a commercial liquid fertiliser (Greenzit ®) is added to the water. The test is evaluated 12 days after sowing and the action on the plants is assessed.

In this test, the test compounds of Table 1 exhibit strong herbicidal activity.

EXAMPLE 9

Herbicidal action in wild rice (paddy)

Selective herbicidal action in transplanted rice

Twenty-five-day-old rice plants are transplanted into large rectangular asbestos cement containers in a greenhouse. Seeds of the weeds occurring in rice crops, namely Echniochloa crus galli, Scirpus sp., Monocharia vaginalis and Sagittaria pygmea, are then sown between the rows of rice plants. The containers are well watered and kept at a temperature of about 25° C. and at high humidity. Twelve days later, when the weeds have emerged and reached the 2–3 leaf stage, the soil in each of the containers is covered with a layer of water to a height of 2.5 cm. The test compounds are then applied in the form of emulsificable concentrates with a pipette between the rows of plants. Each emulsifiable concentrate is diluted and applied such that it corresponds to a concentration of test compound of 1 and ½ kg/ha respectively. The test is evaluated 4 weeks later and the state of the plants is assessed in accordance with the above rating.

The results are shown in Table 3.

TABLE 3

| Plant Concentration kg/ha | Rice 1 | Rice ½ | Echinochloa crus galli 1 | Echinochloa crus galli ½ | Scripus 1 | Scripus ½ | Monocharia vaginalis 1 | Monocharia vaginalis ½ |
|---|---|---|---|---|---|---|---|---|
| Compound | | | | | | | | |
| 1.001 | 7 | 8 | 1 | 1 | 1 | 1 | 7 | 8 |
| 1.010 | 9 | 9 | 1 | 3 | 3 | 6 | 6 | 6 |
| 1.014 | 8 | 9 | 1 | 1 | 2 | 4 | 7 | 9 |
| 1.018 | 9 | 9 | 2 | 3 | 1 | 1 | 3 | 5 |

TABLE 3-continued

| Plant Concentration kg/ha | Rice | | Echinochloa crus galli | | Scripus | | Monocharia vaginalis | |
|---|---|---|---|---|---|---|---|---|
| | 1 | ½ | 1 | ½ | 1 | ½ | 1 | ½ |
| 1.020 | 9 | 9 | 1 | 4 | 5 | 7 | 8 | 9 |
| 1.028 | 9 | 9 | 1 | 1 | 1 | 1 | 3 | 4 |
| 1.029 | 9 | 9 | 1 | 1 | 1 | 1 | 2 | 5 |
| 1.031 | 9 | 9 | 1 | 1 | 1 | 3 | 1 | 4 |
| 1.032 | 9 | 9 | 1 | 1 | 1 | 1 | 1 | 1 |
| 1.033 | 9 | 9 | 1 | 2 | 2 | 3 | 7 | 8 |
| 1.035 | 9 | 9 | 1 | 1 | 2 | 5 | 4 | 6 |
| 1.036 | 6 | 6 | 1 | 1 | 1 | 1 | 1 | 1 |
| 1.037 | 6 | 7 | 1 | 1 | 1 | 1 | 1 | 2 |
| 1.038 | 9 | 9 | 1 | 1 | 1 | 1 | 1 | 3 |
| 1.040 | 8 | 9 | 1 | 1 | 1 | 1 | 3 | 5 |
| 1.042 | 8 | 9 | 1 | 1 | 1 | 2 | 3 | 5 |
| 1.051 | 7 | 8 | 1 | 1 | 3 | 5 | 6 | 8 |
| 1.057 | 9 | 9 | 1 | 1 | 1 | 1 | 1 | 4 |
| 1.058 | 8 | 9 | 1 | 1 | 1 | 1 | 3 | 6 |
| 1.073 | 7 | 8 | 1 | 1 | 1 | 1 | 1 | 1 |
| 1.103 | 7 | 8 | 1 | 1 | 1 | 3 | 4 | 8 |
| 1.105 | 7 | 8 | 1 | 1 | 1 | 1 | 1 | 3 |
| 1.106 | 9 | 9 | 1 | 1 | 5 | 7 | 9 | 9 |
| 1.112 | 9 | 9 | 1 | 1 | 2 | 4 | 7 | 9 |
| 1.114 | 9 | 9 | 1 | 2 | 1 | 3 | 7 | 9 |
| 1.115 | 8 | 9 | 1 | 1 | 2 | 3 | 2 | 3 |
| 1.118 | 6 | 8 | 1 | 1 | 1 | 1 | 1 | 4 |
| 1.121 | 7 | 9 | 1 | 1 | 1 | 3 | 7 | 9 |
| 1.123 | 9 | 9 | 1 | 1 | 2 | 4 | 9 | 9 |
| 1.124 | 8 | 9 | 1 | 1 | 1 | 2 | 8 | 9 |
| 1.129 | 8 | 9 | 1 | 1 | 2 | 4 | 6 | 7 |
| 1.130 | 9 | 9 | 1 | 1 | 1 | 2 | 5 | 6 |
| 1.133 | 9 | 9 | 1 | 1 | 1 | 1 | 4 | 6 |
| 1.134 | 9 | 9 | 1 | 1 | 3 | 5 | 3 | 5 |
| 1.136 | 9 | 9 | 1 | 1 | 4 | 4 | 4 | 6 |
| 1.137 | 8 | 9 | 1 | 1 | 1 | 1 | 2 | 4 |
| 1.138 | 9 | 9 | 1 | 1 | 1 | 2 | 1 | 3 |
| 1.139 | 9 | 9 | 1 | 1 | 1 | 4 | 4 | 6 |
| 1.140 | 9 | 9 | 1 | 1 | 1 | 1 | 6 | 7 |
| 1.141 | 9 | 9 | 1 | 2 | 1 | 4 | 8 | 9 |
| 1.142 | 9 | 9 | 1 | 1 | 1 | 2 | 5 | 6 |
| 1.143 | 9 | 9 | 1 | 1 | 2 | 3 | 5 | 6 |
| 1.144 | 6 | 6 | 1 | 1 | 1 | 1 | 2 | 3 |

The test compounds severely damage the weeds, but cause either negligible or no damage to the rice.

EXAMPLE 10

Growth inhibition of tropical leguminous cover crops

The test plants (Centrosema plumieri and Centrosema pubescens) are reared until fully grown and then cut back to a height of 60 cm. The plants are sprayed 7 days later with an aqueous emulsion of the test compound. The test plants are kept at 70% relatively humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test, a marked reduction in new growth of the plants treated with compounds of Table 1 at concentrations of 50 to 3000 g/ha is observed (less than 20% of the newgrowth of untreated control plants), without damage being caused to the test plants.

EXAMPLE 11

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 100 g a.i. per hectare. Evaluation is made about 5 weeks after application. Compared with untreated controls, the compounds of Table 1 of the invention markedly increase the number and weight of the harvested siliquae on the leading shoot.

EXAMPLE 12

Growth inhibition of cereals

Summer barley (Hordeum vulgare) and summer rye (Secale) are sown in sterilised soil in plastic pots in a greenhouse and watered as required. The cereal shoots are treated about 21 days after sowing with an aqueous spray mixture of a compound of Table 1. The concentration corresponds to up to 100 g of active ingredient per hectare. Evaluation of the growth of the cereals is made 21 days after application. A comparison with untreated controls shows that the new growth of treated cereal plants is reduced (60–90% of the controls) and that the diameter of the stalks has in some cases increased.

EXAMPLE 13

Growth inhibition of grasses

Seeds of the grasses Lolium perenne, Poa pratensis, Festuca ovina, Dactylis glomerate and Cynodon dactylon are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of Table 1. The concentraion of test compound corresponds to a rate of application of up to 500 g a.i. per hectare. The growth of the grasses is evaluated 21 days after application. The test compounds of formula I effect a reduction in new growth in the range of 10–30% in comparison with untreated controls.

What is claimed is:

1. A herbicidal and plant growth regulating composition which contains as active ingredient an effective amount of a 2-benzoyl-2-phenyloxirane of formula I

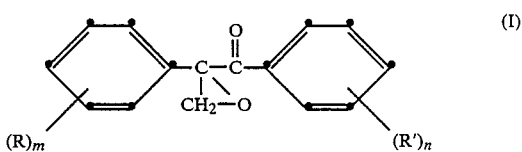

wherein each of m and n independently of the other is 0, 1, 2 or 3 and each of R and R' independently of the other is a halogen atom, a $C_1$-$C_4$alkyl, $C_1$-$C_4$alkoxy, $C_1$-$C_4$haloalkyl or $C_1$-$C_4$ haloalkoxy group or the nitro or cyano group or a phenoxy group which is substituted by $(R)_m$, in the form of a racemate or an optically active enantiomer, together with inert adjuvants selected from (a) solid carriers with or without surfactants and (b) liquid carriers plus effective amounts of surfactants.

2. A composition according to claim 1, which contains as active ingredient a 2-benzyl-2-phenyxloxirane of formula I according to claim 1, wherein each of m and n independently of the other is 0, 1, 2 or 3 and each of R and R' independently of the other is fluorine, chlorine, bromine, methyl, methoxy or trifluoromethyl, or R is also a phenixoy group which is substituted by $(R)_m$.

3. A composition according to claim 1, which contains as active ingredient a 2-benzyl-2-phenyxloxirane of formula I according to claim 1, wherein each of m and n independently of the other is 0, 1, 2 or 3 and each of R and R' independently of the other is fluorine, chlorine, methyl, methoxy or trifluoromethyl.

4. A composition according to claim 1, which contains as active ingredient 2-benzoyl-2-phenyloxirane.

5. A composition according to claim 1, which contains as active ingredient 2-benzoyl-2-(4-bromophenyl)oxirane.

6. A composition according to claim 1, which contains as active ingredient 2-(4-chlorobenzoyl)-2-(4-chlorophenyl)oxirane.

7. A composition according to claim 1, which contains as active ingredient 2-(4-chlorobenzoyl)-2-(2-chlorophenyl)oxirane.

8. A composition according to claim 1, which contains as active ingredient 2-benzoyl-2-m-tolyoxirane.

9. A composition according to claim 1, which contains as active ingredient 2-(2-chlorobenzoyl)-2-phenyloxirane.

10. A composition according to claim 1, which contains as active ingredient 2-(4-chlorobenzoyl)-2-(3-chlorophenyl)oxirane.

11. A composition according to claim 1, which contains as active ingredient 2-(B 4-chlorobenzoyl)-2-(3-bromophenyl)oxirane.

12. A composition according to claim 1, which contains as active ingredient 2-(4-chlorobenzoyl)-2-phenyloxirane.

* * * * *